United States Patent

Noiles et al.

[11] Patent Number: 5,549,694
[45] Date of Patent: Aug. 27, 1996

[54] ACETABULAR PROSTHESIS WITH APERTURES SEALED WITH DEFORMABLE DISCS AND METHOD

[75] Inventors: Douglas G. Noiles, New Canaan; Alfred F. DeCarlo, Jr., Stamford, both of Conn.

[73] Assignee: Joint Medical Products Corporation, Stamford, Conn.

[21] Appl. No.: 280,592

[22] Filed: Jul. 25, 1994

[51] Int. Cl.$^6$ ...................................................... A61F 2/34
[52] U.S. Cl. ................................................ 623/22; 623/18
[58] Field of Search .................................. 623/16, 18, 19, 623/20, 22, 23; 29/447

[56] References Cited

U.S. PATENT DOCUMENTS

| | | | |
|---|---|---|---|
| 4,001,928 | 1/1977 | Schweiso | 29/447 |
| 4,883,491 | 11/1989 | Mallory et al. | |
| 4,944,759 | 7/1990 | Mallory et al. | |

*Primary Examiner*—David Isabella
*Attorney, Agent, or Firm*—Maurice M. Klee

[57] ABSTRACT

An acetabular cup for use with a plastic socket bearing is provided. The cup includes a circular aperture having a stepped configuration. A domed disc is inserted in the aperture and deformed to seal the aperture. In this way, plastic particles, which are generated by wear of the bearing during use, are prevented from migrating through the aperture to the bone surrounding and supporting the prosthesis.

8 Claims, 1 Drawing Sheet

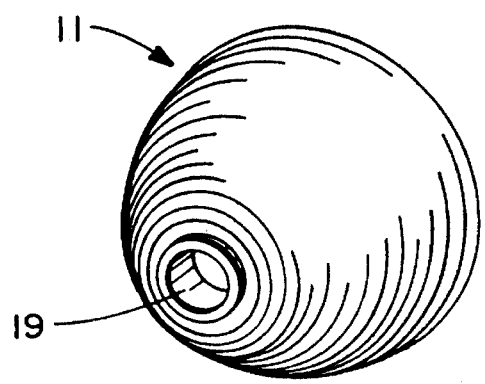
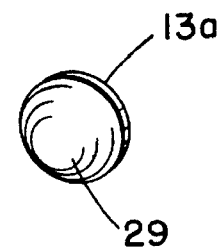
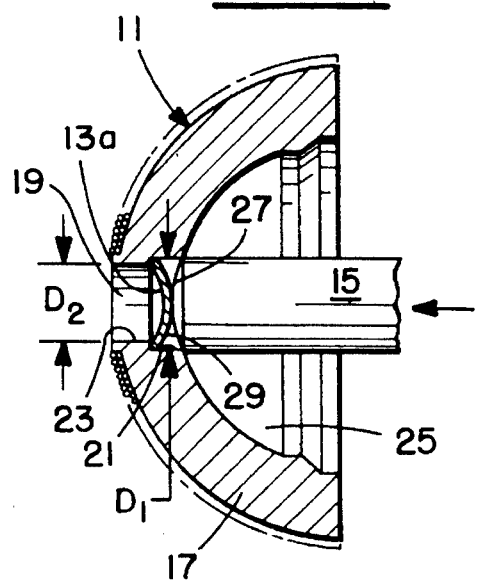
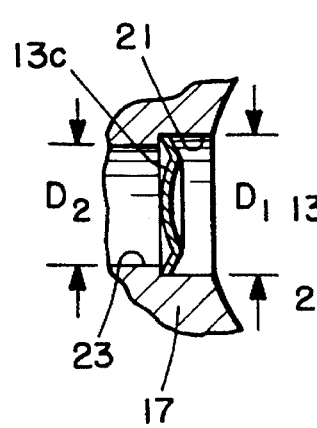
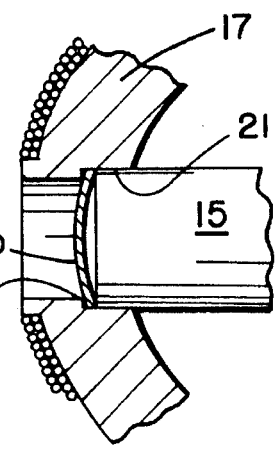
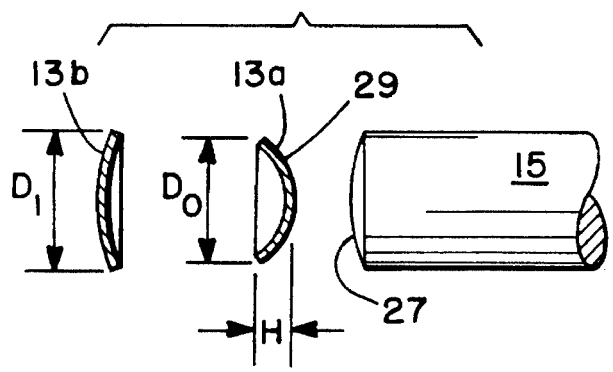
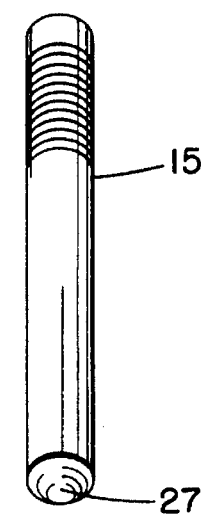

ACETABULAR PROSTHESIS WITH APERTURES SEALED WITH DEFORMABLE DISCS AND METHOD

BACKGROUND OF THE INVENTION

1. Field of the Invention

This invention relates to acetabular prostheses and, in particular, to two-part acetabular prostheses which have a metal cup and a plastic socket bearing.

2. Description of the Prior Art

Numerous two-part acetabular prostheses having a metal cup and a plastic socket bearing are known. See, for example, Mallory et al., U.S. Pat. Nos. 4,883,491 and 4,944,759. A common feature of many of these prostheses is an aperture at the apex of the metal cup, which is provided to aid the surgeon in the implantation process.

As a result of wear, plastic bearings are known to generate submicron particles in the body. These particles are believed to lead to cell lysis and ultimate resorption of bone surrounding and supporting the acetabular prosthesis. Studies have shown that plastic particles accumulate around the periphery of the face of the acetabular cup, as well as in the area of the apical aperture. The present invention is directed to a practical system for eliminating access of these particles to the bone through the apical aperture.

SUMMARY OF THE INVENTION

To address the plastic particle problem, the invention provides an acetabular cup which has a circular aperture composed of a first portion and a second portion. The first portion is accessible from the interior of the cup and has a cross-section having a diameter $D_1$. The second portion is contiguous with the first portion, is located radially (axially) outward from the first portion, and has a diameter $D_2$, which is smaller than $D_1$.

The invention further provides a domed disc of a deformable material, e.g., metal, having an undeformed height H and an undeformed maximum outside diameter $D_0$, which is smaller than $D_1$ and larger than $D_2$. Using this disc, the aperture is sealed by inserting the disc in the first portion of the aperture and deforming the disc by reducing the height H and thereby increasing the disc's maximum outside diameter so that the disc is compressively locked in the aperture. In this way, migration of particles through the aperture is prevented.

BRIEF DESCRIPTION OF THE DRAWINGS

FIG. 1 is a perspective view of an acetabular cup having an apical aperture.

FIG. 2 is a perspective view of a deformable disc for use in sealing the aperture.

FIG. 3 is a cross-sectional view of an acetabular cup showing the deformable disc in position for sealing the aperture. The figure also shows a tool in position for deforming the disc.

FIG. 4 is an enlarged, cross-sectional view of the apex of the cup showing the deformable disc after deformation.

FIG. 4A shows an alternate pattern of deformation of the deformable disc.

FIG. 5 is a schematic diagram illustrating the principle of the invention.

FIG. 6 is a perspective view of the tool shown in FIGS. 3, 4, and 5.

The foregoing drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

The reference numbers used in the drawings correspond to the following:

11 acetabular cup
13a deformable disc prior to deformation
13b deformable disc after deformation
13c deformable disc after alternate deformation
15 deformation tool
17 body of acetabular cup
19 aperture
21 first portion of aperture
23 second portion of aperture
25 interior of acetabular cup
27 convex surface of deformation tool
29 convex surface of deformable disc prior to deformation

DESCRIPTION OF THE PREFERRED EMBODIMENTS

With reference to the drawings, wherein like reference characters designate like or corresponding parts throughout the several views, there is shown in FIG. 1 an acetabular cup 11 having an apical aperture 19. As shown in FIGS. 3 and 4, aperture 19 includes first portion 21 and second portion 23.

First portion 21 is accessible from the interior of the cup and has a cross-section of diameter $D_1$. Preferably, first portion 21 has straight sides, although other configurations can be used if desired. For the straight side configuration, all cross-sections have diameter $D_1$. For other configurations, the cross-section having a diameter $D_1$ will be at the position at which disc 13 seats when deformed.

Second portion 23 is contiguous with first portion 21 and is located radially outward from the first portion. This portion has a diameter $D_2$, which is smaller than $D_1$. For purposes of illustration, portion 23 is shown as having a longer axial dimension than portion 21 in the figures. In practice, it is preferred to make portion 23 relatively short, e.g., on the order of 1–2 millimeters, so as to provide maximum purchase for an insertion tool (not shown), which engages with portion 21 during implantation of the cup.

Domed disc 13 is used to seal the aperture. The disc is made of a deformable material, such as plastic or metal, with metal being preferred. A particularly preferred metal is a soft, chemically pure titanium (grade 1). In practice, this chemically pure titanium has been found to work successfully with cups made of a Ti—6Al—4V alloy. Other materials can, of course, be used if desired.

FIG. 2 shows disc 13 in its undeformed state, identified by the reference number 13a. In this condition, the disc has a height H and a maximum outside diameter $D_0$, which is smaller than $D_1$ and larger than $D_2$. H and $D_0$ are chosen so that the discs if flattened when nonconstrained, will have a diameter sufficiently larger than $D_1$ so as to form a compressive seal when constrained to $D_1$.

In practice, the following dimensions for disc 13, when made of the chemically pure titanium discussed above, have been found to provide the desired compressive seal when used with an aperture having a first portion 21 of diameter $D_1$ equal to 0.501±0.001 inches: $D_0$=0.497±0.001 inches; H=0.065±0.005 inches; disc thickness=0.014±0.001 inches. When flattened, such a disc has a nonconstrained diameter of 0.507±0.001 inches. The 0.006 inch difference between the constrained and nonconstrained diameters results in a substantial compressive force on the disc when deformed in first portion 21 of aperture 19. A suitable dimension for $D_2$ for use with this disc is 0.460±0.005 inches.

As shown in FIG. 3, disc 13a in its undeformed state is inserted into first portion 21 of aperture 19 with its convex side 29 facing the interior of the cup. Thereafter, tool 15, which has a convex working surface 27, is inserted into the first portion 21 and brought into engagement with the convex side of the disc. A mallet blow to tool 15 causes disc 13a to deform and snap into deformed shape 13b, wherein the disc forms a compressive seal with the walls of first portion 21. Under certain combinations of tolerances, the deformed disc may buckle to assume a wavy configuration of the type identified by the reference number 13c in FIG. 4A. In this condition, there is also sufficient interference between the disc and the aperture to form a compressive seal.

Although specific embodiments of the invention have been described and illustrated, it is to be understood that modifications can be made without departing from the invention's spirit and scope. For example, although illustrated for the case of an aperture located at the apex of an acetabular cup, the invention can also be used to seal apertures located elsewhere on the surface of the cup. Also, the invention can be used in a two part acetabular cup where the socket bearing is made of a material other than plastic, e.g., metal or ceramic. A variety of other modifications which do not depart from the scope and spirit of the invention will be evident to persons of ordinary skill in the art from the disclosure herein. The following claims are intended to cover the specific embodiments set forth herein as well as such modifications, variations, and equivalents.

What is claimed is:

1. An acetabular cup for receiving a bearing, said cup comprising:

a body having an interior surface for receiving the bearing, an exterior surface for engaging bone, and a circular aperture which passes through the body from the interior surface to the exterior surface, said aperture having:

(a) a first portion, which is accessible from the interior of the body and has a cross-section having a diameter $D_1$, and (b) a second portion, which is contiguous with the first portion, is located radially outward from the first portion, and has a diameter $D_2$ that is smaller than $D_1$; and a deformable disc compressively locked within said aperture so as to seal the aperture, said disc;

(i) prior to insertion in said aperture, having a concave side, a convex side, and a diameter which is smaller than $D_1$ and larger than $D_2$, (ii) being inserted into the aperture from the interior of the body with its convex side oriented toward the interior of the body, and (iii) being buckled as a result of having been deformed so as to have a convex portion oriented toward the exterior of the body.

2. The acetabular cup of claim 1 wherein the deformable disc is made of metal.

3. The acetabular cup of claim 1 wherein the aperture is at the apex of the cup.

4. A method for sealing a circular aperture in an acetabular cup, said aperture having a first portion, which is accessible from the interior of the cup and has a cross-section having a diameter $D_1$, and a second portion, which is contiguous with the first portion, is located radially outward from the first portion, and has a diameter $D_2$ that is smaller than $D_1$, said method comprising:

(a) inserting a domed disc of a deformable material in the first portion at said cross-section, said domed disc having a height H and an undeformed maximum outside diameter $D_0$, said undeformed maximum outside diameter being smaller than $D_1$ and larger than $D_2$; and (b) deforming the disc by reducing the height H and thereby increasing the disc's maximum outside diameter so that the disc is compressively locked in the first portion of the aperture at diameter $D_1$.

5. The method of claim 4 wherein the deformable material is metal.

6. The method of claim 4 wherein the disc is inserted in the first portion of the aperture with the disc's convex side facing the interior of the cup.

7. The method of claim 4 wherein the deforming is performed with a tool having a convex surface which engages the disc.

8. The method of claim 4 wherein the aperture is located at the apex of the cup.

* * * * *